(12) United States Patent
Ludwig et al.

(10) Patent No.: US 9,371,220 B2
(45) Date of Patent: Jun. 21, 2016

(54) MICROMECHANICAL COMPONENT, MANUFACTURING METHOD FOR A MICROMECHANICAL COMPONENT AND METHOD FOR MOUNTING A MICROMECHANICAL COMPONENT

(71) Applicants: Matthias Ludwig, Moessingen (DE); Martin Rojahn, Tuebingen (DE)

(72) Inventors: Matthias Ludwig, Moessingen (DE); Martin Rojahn, Tuebingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 233 days.

(21) Appl. No.: 14/281,374

(22) Filed: May 19, 2014

(65) Prior Publication Data

US 2014/0338460 A1    Nov. 20, 2014

(30) Foreign Application Priority Data

May 17, 2013   (DE) .......................... 10 2013 209 248

(51) Int. Cl.
| | |
|---|---|
| *G01L 9/00* | (2006.01) |
| *B81B 7/00* | (2006.01) |
| *B81C 1/00* | (2006.01) |
| *G01N 33/00* | (2006.01) |
| *G01L 13/00* | (2006.01) |
| *G01L 19/00* | (2006.01) |

(52) U.S. Cl.
CPC ............. *B81B 7/0029* (2013.01); *B81B 7/0061* (2013.01); *B81C 1/00341* (2013.01); *G01L 9/00* (2013.01); *G01L 13/00* (2013.01); *G01L 19/0007* (2013.01); *G01N 33/00* (2013.01); *B81B 2201/0264* (2013.01); *B81C 2203/0154* (2013.01); *Y10T 29/49826* (2015.01)

(58) Field of Classification Search
None
See application file for complete search history.

(56) References Cited

U.S. PATENT DOCUMENTS

| | | | | |
|---|---|---|---|---|
| 5,019,301 A | * | 5/1991 | Coden ................. | G02B 6/2804 264/1.25 |
| 5,109,448 A | * | 4/1992 | Coden ................. | G02B 6/2804 264/1.28 |
| 2007/0018301 A1 | * | 1/2007 | Fukuda ................ | B81B 7/0077 257/686 |
| 2010/0203676 A1 | * | 8/2010 | Theuss ................. | H01L 21/561 438/109 |
| 2015/0131100 A1 | * | 5/2015 | Reck ....................... | G01L 11/02 356/445 |

FOREIGN PATENT DOCUMENTS

| | | |
|---|---|---|
| DE | 102009027995 | 1/2011 |
| DE | 102012218929 | 4/2014 |

* cited by examiner

*Primary Examiner* — Andre Allen
(74) *Attorney, Agent, or Firm* — Norton Rose Fulbright US LLP (57) ABSTRACT

A micromechanical component having a sensor chip is described, on and/or in which at least one sensor element is disposed, and a cladding, formed of an injection-molding material, encloses the sensor chip in such a way that at least one partial area of a surface of the sensor chip is covered in airtight fashion by the injection-molding material. At least one channel is formed in the injection-molding material, which takes a course, straight or not straight, from an outer surrounding area of the cladding toward the at least one sensor element of such a length that a change in shape and/or a change in chemical consistency of at least one part of the at least one sensor element is able to be brought about as a function of at least one physical property and/or at least one chemical partial composition of a medium present in the at least one channel.

15 Claims, 5 Drawing Sheets

MICROMECHANICAL COMPONENT, MANUFACTURING METHOD FOR A MICROMECHANICAL COMPONENT AND METHOD FOR MOUNTING A MICROMECHANICAL COMPONENT

FIELD OF THE INVENTION

The present invention relates to a micromechanical component. The invention likewise relates to a manufacturing method for a micromechanical component. In addition, the invention relates to a method for mounting a micromechanical component in a vehicle.

BACKGROUND INFORMATION

German Published Patent Appln. No. 10 2009 027 995 describes a device having a semiconductor component and a housing, as well as a method for manufacturing the device. The housing of the device has at least one electrical connection and at least one fastening point. In addition, the housing includes a first cladding made of thermosetting plastic which essentially surrounds the semiconductor component. Optionally, the first cladding may be surrounded by a second cladding made of thermoplastic or thermosetting plastic.

In German Patent Appln. No. 10 2012 218 929 not prepublished and known internally to the Applicant, a sensor device is described. The sensor device includes an LGA (Land Grid Array) having micromechanical components for detecting physical quantities, which is held with the aid of inserts. The inserts are also intended to be usable as electrical contact elements for the LGA. An inset molding of thermosetting plastic material is intended to provide an additional mechanical fixation of the LGA. In addition, holes are formed in a pre-insert molding and in a screw-shaped fastening element surrounding the LGA, which are intended to permit an exchange of gas, e.g., for the escape of air upon inserting material, or to permit a pressure measurement in a cavity of the fastening element.

SUMMARY

The present invention provides a micromechanical component, a manufacturing method for a micromechanical component, and a method for mounting a micromechanical component in a vehicle.

The present invention makes it possible to reliably protect elements on the at least one partial area of the at least one surface of the sensor chip with the aid of the airtight covering by the cladding formed from the injection-molding material. In this way, the elements worth being protected may be shielded especially from contact with dirt particles and/or liquids. The protection of the at least one element on the at least one partial area of the at least one surface of the sensor chip able to be realized in this manner may significantly increase the operating time/service life of the micromechanical component. At the same time, owing to the formation of the at least one channel in the injection-molding material, good sensitivity of the at least one sensor element continues to be ensured. Thus, the airtight covering of the at least one partial area of the at least one surface of the sensor chip has no unwanted effects on the accuracy in detecting the at least one physical property and/or the at least one chemical partial composition of the medium at least partially surrounding the micromechanical component.

As explained in greater detail below, the present invention provides a micromechanical component which is able to be produced easily and inexpensively. Accordingly, easily executable (standard-compliant) method steps may be used to carry out the manufacturing method of the present invention, whereby even if the micromechanical component is massproduced, favorable quality of the micromechanical components produced is ensured.

In one advantageous specific embodiment, the at least one channel formed in the injection-molding material at least partially exposes at least one side of the at least one sensor element. Thus, in spite of an airtight covering of the at least one partial area of the at least one surface of the sensor chip by the injection-molding material, a direct contact between the medium present in the at least one channel and the at least one sensor element is ensured. This direct contact may contribute to an increase in accuracy in the detection of the at least one physical property and/or the at least one chemical partial composition of the medium present in the at least one channel.

In one advantageous further refinement, at least two channels formed in the injection-molding material at least partially expose the at least one sensor element on two opposite sides. The sensor element at least partially exposed at the two respective opposite sides may be used, in particular, for comparison measurements/comparison analyses. An advantageous example for a comparison measurement/comparison analysis able to be carried out using such a sensor element is explained below.

In a further advantageous specific embodiment, the at least one channel formed in the injection-molding material takes a course, straight or not straight, toward the at least one sensor element of such a length that the at least one sensor element at least remains covered at at least one end of the at least one channel by a membrane of injection-molding material. The at least one sensor element is able to be additionally protected by the membrane of injection-molding material realized in this manner. At the same time, the respective membrane of injection-molding material may be made so thin that advantageous sensitivity of the at least one sensor element continues to be ensured.

For instance, the injection-molding material may be sprayed on the sensor chip. The at least one channel may be formed in the cladding either during the injection-molding process or after that. In both cases, the desired airtight covering of the at least one partial area of the at least one surface of the sensor chip by the injection-molding material is reliably ensured for a micromechanical component manufactured in this manner.

As an alternative, the cladding of injection-molding material may be produced separately, and the sensor chip may be introduced into the cladding. The at least one channel may be formed in the cladding prior to, during or after introducing the sensor chip into the cladding. A long operating time/service life of the sensor chip is ensured for a micromechanical component produced in such a way.

In one advantageous further development, an outer surface of the cladding made of the injection-molding material is at least partially screw-shaped or bolt-shaped. Thus, a simple and reliable fixation of the micromechanical component is assisted, for example, by a screwing-in process or by a press fit. In particular, very high accuracy of fit of the micromechanical component upon being mounted in a vehicle, for instance, may also be achieved with the aid of the screw shape or bolt shape of the cladding. In addition, an alignment of the micromechanical component in which the micromechanical component preferably should be mounted in order to ensure advantageous operation may also be indicated by the screwshaped or bolt-shaped partial formation/formation of the outer surface of the cladding. Consequently, the risk that the micromechanical component will be mounted incorrectly may be reduced significantly, even when done by an uninformed person.

In a further advantageous specific embodiment, the cladding of injection-molding material is surrounded at least partially by an outer cladding part whose outer side is at least partially screw-shaped or bolt-shaped. The advantages set forth above are realized in this case, as well.

Advantageously, the micromechanical component is a pressure sensor having at least one sensor membrane as the at least one sensor element. As explained in greater detail below, such a pressure sensor may be produced easily and cost-effectively, while at the same time, easily practicable mounting and good measuring accuracy of the pressure sensor are ensured. However, it is pointed out that the possibilities for implementing the micromechanical component are not limited to a pressure sensor.

For instance, the micromechanical component may be an absolute pressure sensor, and a channel may be formed in the cladding of injection-molding material at only one side of the at least one sensor element. As an alternative, the micromechanical component may also be a differential-pressure sensor, and one channel each may be formed in the cladding of injection-molding material at the two respective opposite sides of the at least one sensor element. Both specific embodiments of a pressure sensor are able to be produced easily, mounted easily, and used for the reliable ascertainment of pressure values.

The advantages set forth in the previous paragraphs are also ensured in an implementation of the corresponding manufacturing method for a micromechanical component. The manufacturing method is able to be further refined according to the specific embodiments explained above.

In addition, the corresponding method for mounting a micromechanical component in a vehicle likewise realizes the advantages already explained above.

DETAILED DESCRIPTION

Figure 1:
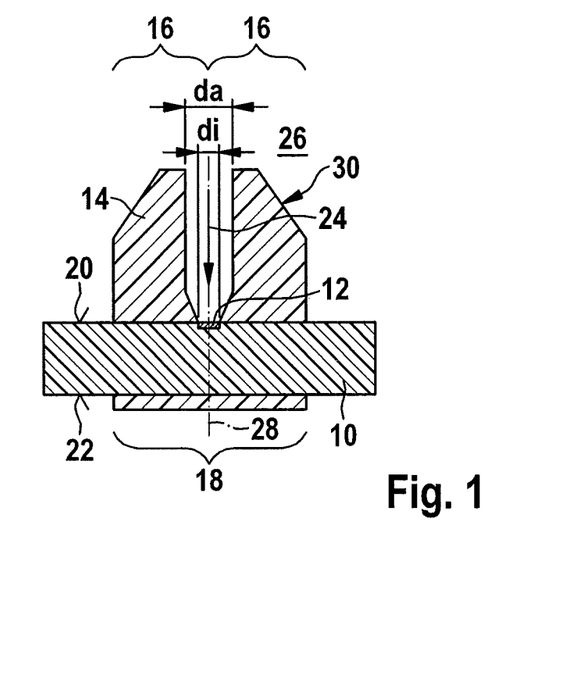
FIG. 1 shows a schematic representation of a first specific embodiment of the micromechanical component.

FIG. 1 shows a schematic representation of a first specific embodiment of the micromechanical component.

The micromechanical component shown schematically in FIG. 1 includes a sensor chip 10, on and/or in which at least one sensor element 12 is disposed. For example, sensor chip 10 may be an LGA (Land Grid Array). In addition to the at least one sensor element 12, at least one further component such as at least one printed circuit trace, for example, may be formed on and/or in sensor chip 10. Since sensor chip 10 is able to be developed with all known sensor-chip components, the further possible components of sensor chip 10 will not be further discussed.

The at least one sensor element 12 is designed in such a way that by a change of shape and/or a change of chemical consistency of at least one part of the at least one sensor element 12, a change is able to be brought about in an electrical property of respective sensor element 12. Preferably, sensor chip 10 is designed in such a way that the change in the electrical property of the at least one sensor element 12 is ascertainable by an evaluation device, disposed on and/or in sensor chip 10 or externally from it, e.g., by the provision of at least one electrical signal. If desired, the evaluation device is designed—taking into account the (directly or indirectly) ascertained change in the electrical property of the at least one sensor element 12—to determine information with regard to at least one physical quantity present in an immediate and/or non-immediate surrounding area of the at least one sensor element 12 and/or to determine a (minimum) concentration of at least one substance in the immediate and/or non-immediate surrounding area of the at least one sensor element 12. It is pointed out that the micromechanical component is not limited to a fitment with a specific sensor element 12. Instead, a multitude of various types of sensor elements 12 may be formed in nearly any number on sensor chip 10 of the micromechanical component.

The micromechanical component has a cladding 14, formed of an injection-molding material, which encloses sensor chip 10 at least partially in such a way that at least one partial area 16 and 18 of at least one surface 20 and 22 of sensor chip 10 is covered in airtight fashion by the injection-molding material. Dependable protection of at least one component lying on the at least one partial area 16 and 18 of sensor chip 10 is reliably ensured by the airtight covering of the at least one partial area 16 and 18 by the injection-molding material. In particular, in this way, components/elements on the at least one partial area 16 and 18 may be protected safely from contamination and/or liquids. In addition, penetration of dirt particles and/or liquids into at least an inner volume of sensor chip 10 may also be prevented in this way. Thus, advantageous cladding 14 may prevent damage to sensor chip 10, which as a rule, helps to increase the operating time/service life of sensor chip 10.

The injection-molding material of cladding 14 is preferably a thermosetting plastic material such as silicone. However, it is pointed out that the possibilities for implementing cladding 14 are not limited to the use of a specific injection-molding material. For example, a thermoplastic material may also be used to form cladding 14. The injection-molding material may be sprayed (directly) onto sensor chip 10. Likewise, cladding 14 of injection-molding material may be produced separately, and sensor chip 10 may (subsequently) be introduced into cladding 14. In both cases, the desired airtight covering of the at least one partial area 16 and 18 by the injection-molding material may be reliably ensured.

At least one channel 24 is formed in the injection-molding material. The at least one channel 24 takes a course, straight or not straight, from an outer surrounding area 26 of cladding 14 toward the at least one sensor element 12 of such a length that the change in shape and/or change in chemical consistency of the at least one part of the at least one sensor element 12 is able to be brought about as a function of at least one physical property and/or at least one chemical partial composition of a medium present in the at least one channel 24. In the specific embodiment in FIG. 1, exactly one channel 24 extends along a single middle longitudinal axis 28 toward the single sensor element 12 of sensor chip 10. Further possible forms/progressions of the at least one channel 24 are described below.

By the formation of the at least one channel 24 in the injection-molding material, an advantageous interaction is realized between the medium present in outer surrounding area 26 and the at least one sensor element 12. Thus, in spite of the fact that sensor chip 10 is surrounded at least partially by cladding 14, thereby ensuring improved protection of sensor chip 10, at the same time, advantageous measuring accuracy/detecting accuracy of the at lest one sensor element 12 is able to be guaranteed. Thus, the at least one sensor element 12 may continue to be used to determine at least one physical property such as a pressure and/or a temperature, and/or to sense an appearance and/or a concentration of at least one substance with high accuracy.

In the specific embodiment in FIG. 1, the at least one channel 24 formed in the injection-molding material at least partially exposes at least one side of the at least one sensor element 12. In this way, a direct contact is able to be produced between the medium in the at least one channel 24 and the at least one sensor element 12 in order to increase detecting accuracy/measuring accuracy. However, advantageous measuring accuracy/detecting accuracy of the at least one sensor element 12 is also ensured if the at least one channel 24 formed in the injection-molding material takes a course, straight or not straight, of such a length toward the at least one sensor element 12 that the at least one sensor element is covered at least partially by a membrane of injection-molding material at at least one end of the at least one channel 24.

Cladding 14 of the micromechanical component in FIG. 1 has a chimney-shaped section 30. In particular, axis 28 may run centrically through chimney-shaped section 30. For example, chimney-shaped section 30 is formed by an outer cone shape at outer surrounding area 26 and an inner cone shape defining the shape of respective channel 24. The outer cone shape may also be defined as frustoconical. In the case of a preferred inner cone shape, at a first end oriented toward outer surrounding area 26, the at least one channel 24 has an outer diameter da, and at a second end oriented toward sensor chip 10/assigned sensor element 12, has a smaller inner diameter di. In each case, the at least one channel 24 is subdividable into an outer section having constant outer diameter da and an inner section having a diameter tapering from outer diameter da to inner diameter di. The result of such a form of chimney-shaped section 30 is that a pressure present in the at least one channel 24 presses cladding 14 more strongly against sensor chip 10. Thus, the pressure present in the at least one channel 24 is able to improve/strengthen the sealing of the at least one partial area 16 and 18 of at least one surface 20 and 22 of sensor chip 10 with the aid of cladding 14. However, the design possibilities of cladding 14 are not limited to a specific form.

In addition, it is pointed out that the advantageous protective action of cladding 14 may also be ensured if it is comparatively small. With the aid of reliably and easily executable processes such as etching processes, for example, the at least one channel 24 may be formed with the desired length and/or form in cladding 14, even if cladding 14 is small. Likewise, with the aid of conventional techniques, it is possible to already form the at least one channel 24 during an injection-molding process to form comparatively small cladding 14.

Figure 2A:
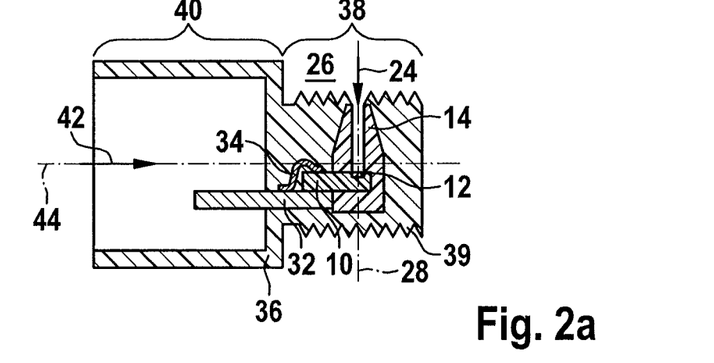
FIGS. 2a to 2c show schematic representations of second, third and fourth specific embodiments of the micromechanical component.
Figure 2B:
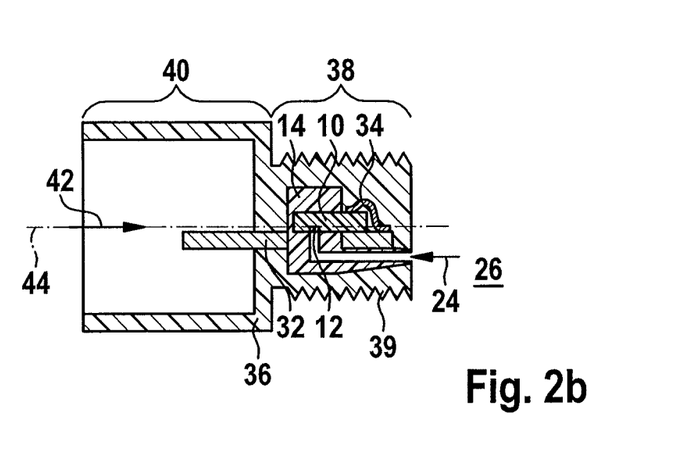
Figure 2C:
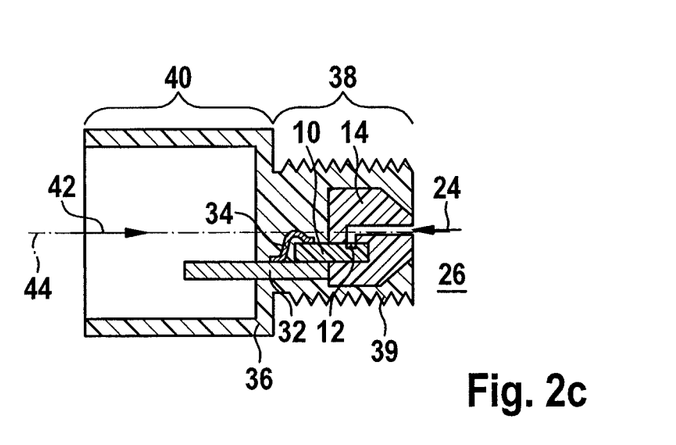

FIG. 2a through 2c show schematic representations of second, third and fourth specific embodiments of the micromechanical component.

Each of the micromechanical components shown schematically in FIG. 2a through 2c takes the form of a pressure sensor having at least one sensor membrane as the at least one sensor element 12. In particular, each of the micromechanical components is an absolute pressure sensor, in each case one channel 24 being formed at only one side of the at least one sensor element 12 in cladding 14 made of the injection-molding material.

In addition, each of the micromechanical components in FIG. 2a through 2c has an electrically conductive insert 32. A mechanical fixation and/or an electrical contacting of assigned sensor chip 10 may be accomplished via each of electrically conductive inserts 32. For example, a sensor chip 10 may be attached by at least one optional metal clip 34 to an electrically conductive insert 32. Due to the advantageous multifunctionality of the at least one metal clip 34 for the fixation of sensor chip 10 and for realizing an electrical contact between sensor chip 10 and adjacent electrically conductive insert 32, wire-bonding joining techniques, printed-circuit-board joining techniques and/or ceramics joining techniques for forming an electrical connection between sensor chip 10 and electrically conductive insert 32 may be omitted. Optionally, electrically conductive insert 32 may also be surrounded at least partially by cladding 14.

Moreover, in the case of each micromechanical component in FIG. 2a through 2c, cladding 14 made of the injection-molding material is surrounded at least partially by an outer cladding part 36 whose outer side is at least partially screw-shaped or bolt-shaped. For example, outer cladding 36 may include a threaded body 38 having a screw thread 39 formed on the outer surface, and an electrical connection socket 40. Sensor chip 10 having cladding 14 may be disposed in threaded body 38 in such a way that the at least one channel 24 is open toward an outer surrounding area of threaded body 38. Likewise, electrically conductive insert 32 may extend at an end directed away from sensor chip 10, as connector contact into a hollow receiving space 42 of electrical connection socket 40.

Outer cladding part 36 may be made of an injection-molding material such as a thermosetting plastic or a thermoplastic, for example. However, the possibilities for the implementation of outer cladding part 36 are not limited to the use of a specific material. Outer cladding part 36 may be produced separately from sensor chip 10 and cladding 14, as well, or may be cast/sprayed at least around sensor chip 10 and cladding 14. Thus, a multitude of reliably and easily executable techniques may be used to form outer cladding 36.

The screw-shaped or bolt-shaped partial formation/formation of outer cladding part 36 facilitates the securing of the micromechanical component. For instance, because of the advantageous formation of outer cladding part 36, the micromechanical component may be fixed reliably in position by a screwing-in process or by a press fit. In addition, the screw-shaped or bolt-shaped partial formation/formation of outer cladding part 36 defines a preferred alignment of the micromechanical component at a preferred installation position. For example, even an uninformed mechanic will place the micromechanical component, furnished with advantageous outer cladding part 36, in such a way that a longitudinal axis 44 of outer cladding part 36 is in a preferred alignment. Moreover, very high accuracy of fit when mounting the micromechanical component, e.g., in a vehicle, is ensured owing to the screw-shaped or bolt-shaped partial formation/formation of outer cladding part 36.

It is pointed out that the advantages described above are also ensured if the outer surface of cladding 14 itself, made of the injection-molding material, is at least partially screw-shaped or bolt-shaped.

In the specific embodiment in FIG. 2a, channel 24 is straight, its single longitudinal axis 28 being aligned perpendicular to longitudinal axis 44 of outer cladding part 36. Channel 24 of the micromechanical component in FIG. 2a is thus open toward a threaded area. In the specific embodiments in FIGS. 2b and 2c, channels 24 in each case are open toward the screw tip and are formed with a bend. Each of channels 24 shown in FIGS. 2b and 2c has an outer section, which is aligned parallel to longitudinal axis 44 of outer cladding part 36, and an inner section running perpendicular to axis 44. With the aid of a bent formation of channels 24, an unwanted penetration of contaminants and/or liquids through channels 24 up to respective assigned sensor element 12 may be additionally prevented. As an alternative to the specific embodiments in FIGS. 2b and 2c, channels 24 may also be bent several times and/or may be at least partially curved. In all the specific embodiments, it is reliably ensured that after the micromechanical component has been mounted, a medium to be analyzed is able to penetrate in the at least one channel 24.

Figure 3A:
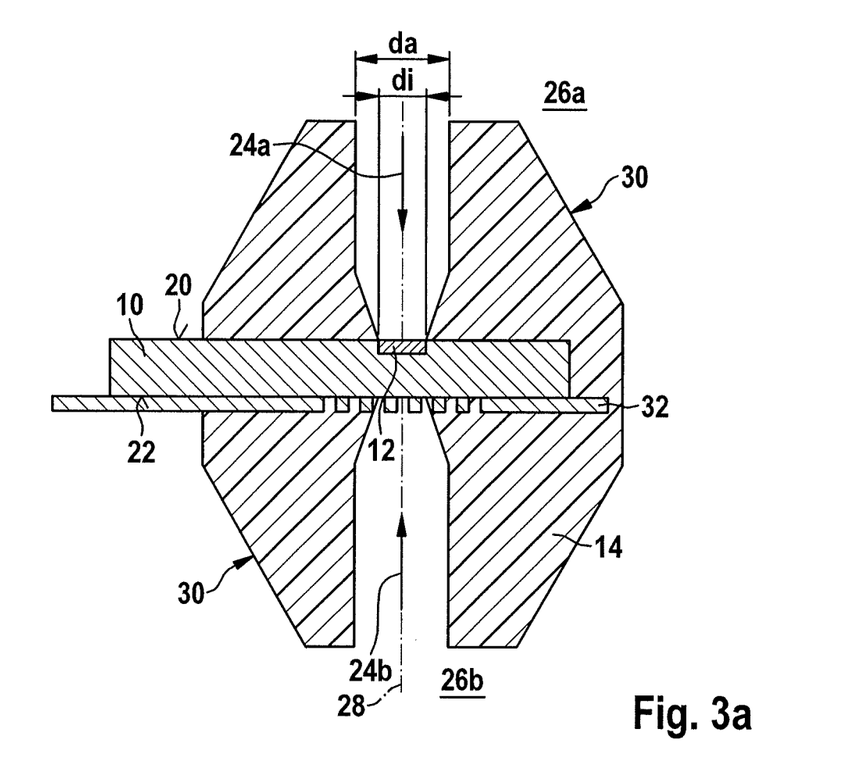
FIGS. 3a and 3b show schematic cross-sections and top views of a fifth specific embodiment of the micromechanical component.
Figure 3B:
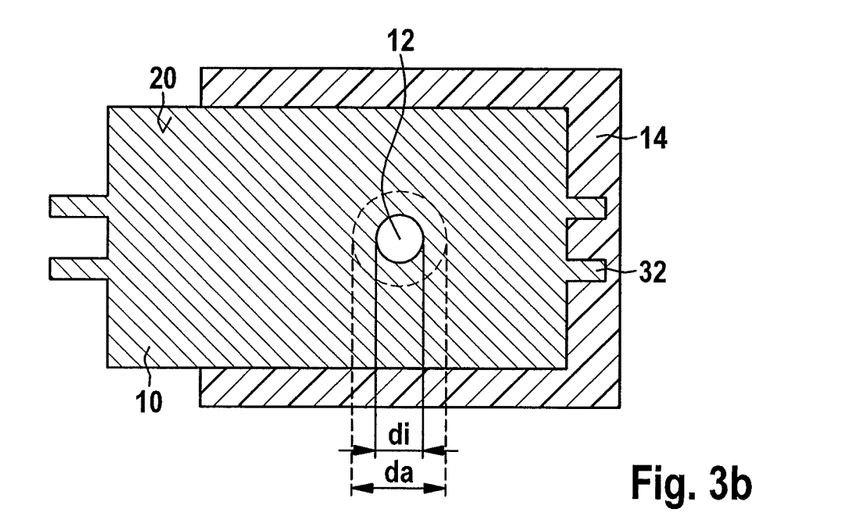

FIGS. 3a and 3b show schematic cross-sections and top views of a fifth specific embodiment of the micromechanical component.

In the case of the micromechanical component shown schematically in FIGS. 3a and 3b, the at least two channels 24a and 24b formed in the injection-molding material at least partially expose the at least one sensor element 12 at two opposite sides. Such a formation of channels 24a and 24b is especially suitable for use of a sensor element 12 taking the form of a sensor membrane in a differential-pressure sensor. Thus, each sensor element 12 has two channels 24a and 24b in the form of pressure-inlet channels. Due to the admission of pressure thus ensured, a difference in pressure existing between surrounding areas 26a and 26b is determinable mechanically with the aid of the at least one sensor element 12. Optionally, channels 24a and 24b assigned to the same sensor element 12 may run along one common axis 28.

Channels 24a and 24b shown schematically in FIG. 3a in each case have outer diameter da at the outside of cladding 14 and inner diameter di at sensor chip 10. Each of channels 24a and 24b has an outer section having constant outer diameter da and an inner section having a diameter tapering from outer diameter da to inner diameter di. Such a form of channels 24a and 24b permits the strengthening/improvement of cohesion between cladding 14 and sensor chip 10 already described above.

Figure 4A:
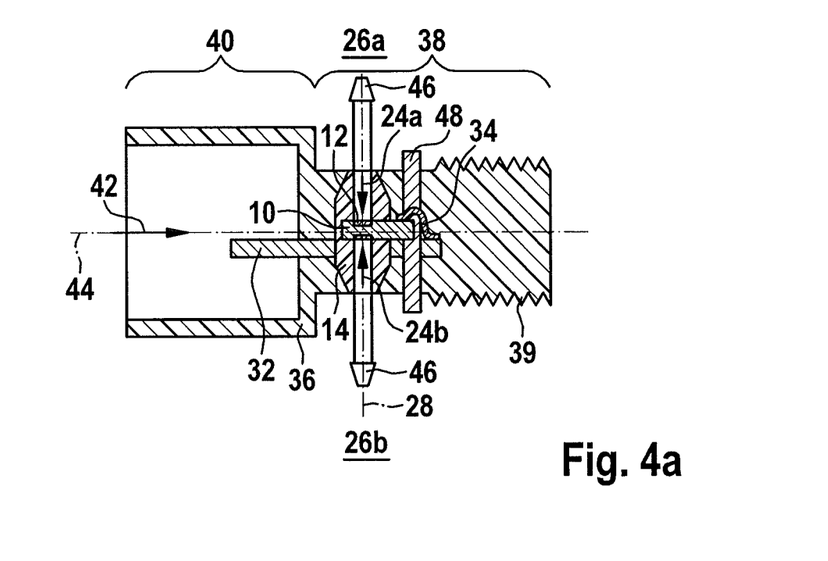
FIGS. 4a and 4b show schematic representations of a sixth and seventh specific embodiment of the micromechanical component.
Figure 4B:
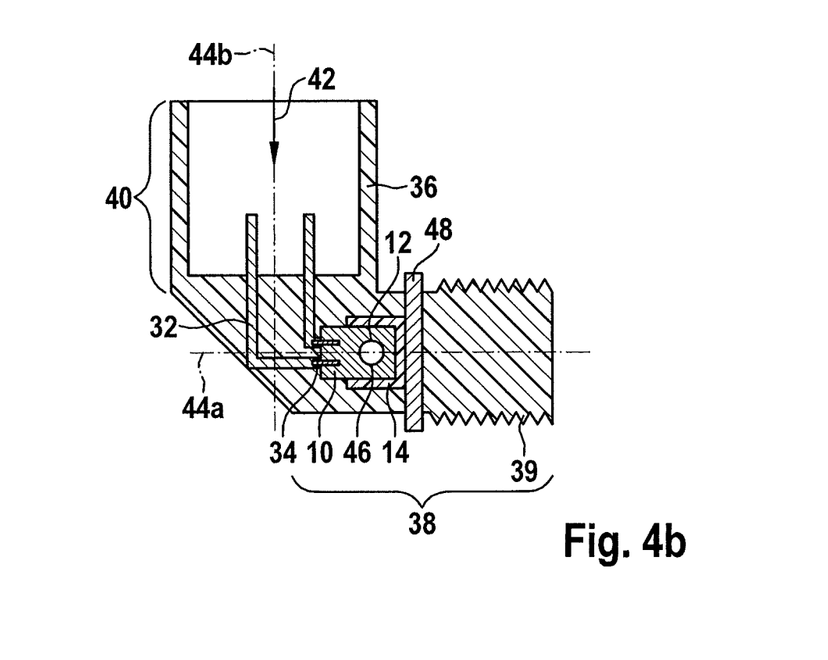

FIGS. 4a and 4b show schematic representations of a sixth and seventh specific embodiment of the micromechanical component.

Each of the micromechanical components shown schematically in FIGS. 4a and 4b is a differential-pressure sensor. One channel 24a and 24b each is formed in cladding 14 of the injection-molding material at the two respective opposite sides of the at least one sensor element 12 of the micromechanical components of FIGS. 4a and 4b. In the case of both micromechanical components in FIGS. 4a and 4b, an alignment of common longitudinal axis 28 of channels 24a and 24b of a sensor element 12 is perpendicular to a longitudinal axis 44 or 44a of at least threaded body 38. Alternatively, channels 24a and 24b at least sectionally may also be formed parallel to and/or inclined by an angle not equal to 90° relative to longitudinal axis 44a of at least threaded body 38, and/or may be curved.

In addition, in the case of the micromechanical components shown in FIGS. 4a and 4b, connectors 46 (shown only in FIG. 4a) are formed at each outer area of channels 24a and 24b.

In each instance, a tube, via which the medium used for the differential-pressure measurement may be introduced, is able to be attached to connectors 46. The specific embodiments described before may also be provided with at least one such connector 46.

The specific embodiments in FIGS. 4a and 4b also have an angle locking device 48. Angle locking device 48 ensures accurately positioned mounting of the micromechanical component, e.g., on a vehicle, and prevents unintended loosening of the screw connection. Reference is made to the German patent application having application number DE 10 2012 21 8901 with regard to a possible form of angle locking device 48.

In particular, angle locking device 48 may lie between screw thread 39 and a section of screw body 38 cut/passed through by channels 24a and 24b formed in it. Screw thread 39 may thus be dimensioned independently of screw body 38.

FIG. 4b shows a further refinement, in which electrical connection socket 40 is oriented at an angle relative to threaded body 38. This may also be described to the effect that a longitudinal axis 44a of threaded body 38 is aligned perpendicular to a longitudinal axis 44b of electrical connection socket 40.

All specific embodiments described above may be used as detached low-pressure sensors for measuring absolute or differential pressure. The pressure sensors able to be realized in this manner are smaller and able to be mounted more easily compared to conventional sensors. Therefore, in the case of the micromechanical components described above, the advantages of LGA packaging are ensured simultaneously with the advantages of the thermoplastic housing in screw form.

Figure 5:
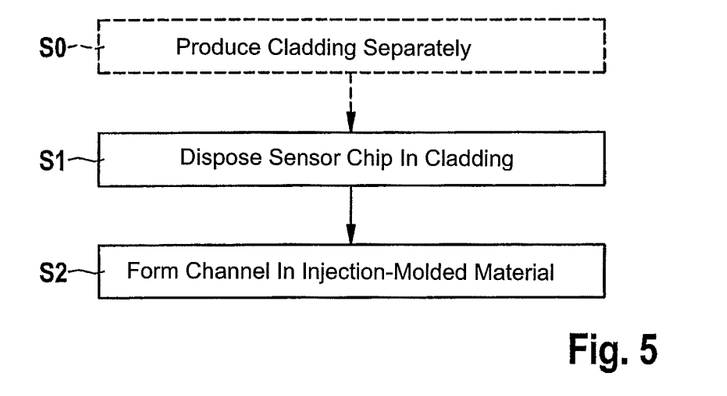
FIG. 5 shows a flow chart for explaining a specific embodiment of the manufacturing method for a micromechanical component.

FIG. 5 shows a flow chart for explaining a specific embodiment of the manufacturing method for a micromechanical component.

In a method step S1, a sensor chip, on and/or in which at least one sensor element is located, is disposed in a cladding, formed of an injection-molding material, in such a way that at least one partial area of at least one surface of the sensor chip is covered in airtight fashion by the injection-molding material. In particular, a partial area of the sensor-chip surface at least partially surrounding the at least one sensor element may be covered in airtight fashion in this manner. The cladding surrounds the sensor chip at least partially after its placement in the cladding.

The sensor chip may be placed in the cladding in method step S1 by spraying the injection-molding material (directly) on the sensor chip. The cladding may first be produced separately (in an optional method step S0), as well. The sensor chip may subsequently be introduced into the cladding in method step S1.

The at least one sensor element disposed on the sensor chip is designed in such a way that a change in shape and/or a change in chemical consistency of at least one part of the at least one sensor element brings about a change in an electrical property of the respective sensor element. Examples for the at least one sensor element have already been described above.

The manufacturing method also includes a method step S2, which optionally may be carried out during method step S0, between method steps S0 and S1, during method step S1 or after method step S1. The numbering of method step S2 therefore specifies no time sequence with respect to its execution. In method step S2, at least one channel is formed in the injection-molding material (prior to, during or after the placement of the sensor chip in the cladding). The at least one channel is formed in such a way that the at least one channel takes a course, straight or not straight, from an outer surrounding area of the cladding toward the at least one sensor element of such a length that the change in shape and/or the change in chemical consistency of the at least one part of the at least one sensor element of the finished micromechanical component is produced as a function of at least one physical property and/or at least one chemical partial composition of a medium present in the at least one channel.

Method steps S0, S1 and S2 may be carried out easily, quickly and with the use of standard-compliant processes. Thus, even if the micromechanical component is mass-produced, advantageous quality of the micromechanical components produced is realized at least with the aid of method steps S1 and S2. Reference is made to the explanations above with regard to a further refinement of the manufacturing method described here and the advantages able to be realized with it.

Figure 6:
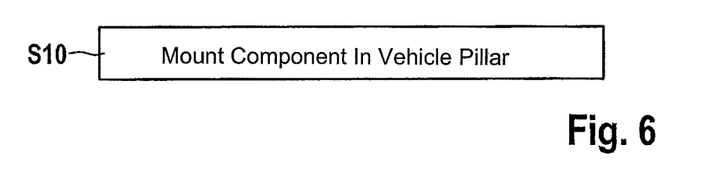
FIG. 6 shows a flow chart for explaining a specific embodiment of the method for mounting a micromechanical component in a vehicle.

FIG. 6 shows a flow chart to explain a specific embodiment of the method for mounting a micromechanical component in a vehicle.

In a method step S10, a micromechanical component is mounted in a vehicle pillar. Reference is made to the descriptions above with regard to possible specific embodiments of the micromechanical component able to be mounted in method step S10. However, it is pointed out that the practicability of method step S10 is not limited to the use of such micromechanical components.

By the method described here for mounting the micromechanical component, use may be made of hollow spaces available in a vehicle pillar, which are present in any case for the strength of the vehicle body, to mount the micromechanical component. Particularly if the micromechanical component is in the form of a pressure sensor, in this way it is possible to reliably measure a pressure present within at least one hollow space in the vehicle. In addition, by the implementation of the method described here, it is possible to save on space in the vehicle interior.

Method step S10 may be carried out to mount the micromechanical component in an A-pillar, a B-pillar or a C-pillar. Mounting the micromechanical component in a B-pillar is preferred. The formation of the cladding or the outer cladding part as a screw or bolt particularly facilitates the mounting of the micromechanical component in a vehicle pillar.

What is claimed is:

1. A micromechanical component, comprising:
   a sensor chip;
   at least one sensor element disposed at least one of on and in the sensor chip, wherein at least one of a change in shape and a change in chemical consistency of at least one part of the at least one sensor element is able to bring about a change in an electrical property of the sensor element; and
   a cladding, formed of an injection-molding material, and enclosing the sensor chip at least partially in such a way that at least one partial area of at least one surface of the sensor chip is covered in airtight fashion by the injection-molding material;
   wherein:
      at least one channel is formed in the injection-molding material,
      the at least one channel takes one of a straight course and a course that is not straight from an outer surrounding area of the cladding toward the at least one sensor element,
      the at least one channel is of such a length that at least one of the change in shape and the change in chemical consistency of the at least one part of the at least one sensor element is able to be brought about as a function of at least one of at least one physical property and at least one chemical partial composition of a medium present in the at least one channel.

2. The micromechanical component as recited in claim 1, wherein the at least one channel formed in the injection-molding material at least partially exposes at least one side of the at least one sensor element.

3. The micromechanical component as recited in claim 2, wherein at least two channels formed in the injection-molding material at least partially expose the at least one sensor element on two opposite sides.

4. The micromechanical component as recited in claim 1, wherein:
   the at least one channel formed in the injection-molding material takes one of a course that is straight and a course that is not straight from the outer surrounding area of the cladding toward the at least one sensor element of such a length that the at least one sensor element remains at least partially covered at at least one end of the at least one channel by a membrane of injection-molding material.

5. The micromechanical component as recited in claim 1, wherein the injection-molding material is sprayed onto the sensor chip.

6. The micromechanical component as recited in claim 1, wherein the cladding of injection-molding material is produced separately, and wherein the sensor chip is introduced into the cladding.

7. The micromechanical component as recited in claim 1, wherein an outer surface of the cladding of injection-molding material is one of at least partially screw-shaped and at least partially bolt-shaped.

8. The micromechanical component as recited in claim 1, wherein the cladding of injection-molding material is surrounded at least partially by an outer cladding part provided with an outer side that is one of at least partially screw-shaped and at least partially bolt-shaped.

9. The micromechanical component as recited in claim 1, wherein the micromechanical component is a pressure sensor having at least one sensor membrane as the at least one sensor element.

10. The micromechanical component as recited in claim 9, wherein the micromechanical component is an absolute pressure sensor, and in each instance, a channel is formed in the cladding of injection-molding material at only one side of the at least one sensor element.

11. The micromechanical component as recited in claim 9, wherein the micromechanical component is a differential-pressure sensor, and one channel each is formed in the cladding of injection-molding material at the two respective opposite sides of the at least one sensor element.

12. A manufacturing method for a micromechanical component, comprising:
   placing a sensor chip in a cladding, wherein:
      at least one sensor element is disposed at least one of on and in the sensor chip,
      a change is brought about in an electrical property of the at least one sensor element is brought about by at least one of a change in shape and a change in chemical consistency of at least one part of the at least one sensor element, and
      the cladding is formed of an injection-molding material and encloses the sensor chip at least partially in such a way that at least one partial area of at least one surface of the sensor chip is covered in airtight fashion by the injection-molding material;

forming at least one channel in the injection-molding material one of prior to, during, and after the placement of the sensor chip in the cladding, wherein:

the at least one channel being formed in such a way that in the completed micromechanical component, the at least one channel takes one of a straight course and a course that is not straight, from an outer surrounding area of the cladding toward the at least one sensor element of such a length that at least one of the change in shape and the change in chemical consistency of the at least one part of the at least one sensor element of the finished micromechanical component is brought about as a function of at least one of at least one physical property and at least one chemical partial composition of a medium present in the at least one channel.

13. The manufacturing method as recited in claim 12, wherein in order to dispose the sensor chip in the cladding, the injection-molding material is sprayed onto the sensor chip.

14. The manufacturing method as recited in claim 12, wherein the cladding of injection-molding material is produced separately, and wherein the sensor chip is introduced into the cladding.

15. A method for mounting a micromechanical component in a vehicle, comprising:

mounting, in a vehicle pillar, one of a micromechanical component as recited in claim 1 and a micromechanical component produced according to a manufacturing method as recited in claim 12.

\* \* \* \* \*